(12) United States Patent
Kimura

(10) Patent No.: US 7,382,461 B2
(45) Date of Patent: Jun. 3, 2008

(54) ANALYSIS METHOD AND APPARATUS UTILIZING ATTENUATED TOTAL REFLECTION

(75) Inventor: Toshihito Kimura, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 350 days.

(21) Appl. No.: 11/077,132

(22) Filed: Mar. 11, 2005

(65) Prior Publication Data
US 2005/0200852 A1 Sep. 15, 2005

(30) Foreign Application Priority Data
Mar. 11, 2004 (JP) .............................. 2004/068959
Feb. 16, 2005 (JP) .............................. 2005-039117

(51) Int. Cl.
*G01N 21/55* (2006.01)
(52) U.S. Cl. .............. 356/445; 250/559.4; 250/559.45; 250/208.1; 348/346
(58) Field of Classification Search ................ 356/445; 250/559.4, 559.45, 208.1
See application file for complete search history.

(56) References Cited

U.S. PATENT DOCUMENTS

| 6,597,456 | B2 | 7/2003 | Kubo et al. |
| 7,061,533 | B1 * | 6/2006 | Urushiya .................... 348/346 |
| 2003/0189707 | A1 * | 10/2003 | Naya et al. ................. 356/445 |
| 2006/0115177 | A1 * | 6/2006 | Ishiga ....................... 382/275 |

FOREIGN PATENT DOCUMENTS

JP 6-167443 A 6/1994

OTHER PUBLICATIONS

Takayuki Okamura, "Surface Refracto-Sensor using Evanescent Waves: Principles and Instrumentations", Spectrum Researches, 1998, pp. 19-28, vol. 47, No. 1.
Knut Johansen, et al., "Surface plasmon resonance: instrumental resolution using photo diode arrays", Measurement Science and Technology, 2000, pp. 1630-1638, vol. 11.

* cited by examiner

*Primary Examiner*—L. G. Lauchman
*Assistant Examiner*—Abdullahi Nur
(74) *Attorney, Agent, or Firm*—Sughrue Mion, PLLC

(57) ABSTRACT

An image of a light beam, which has been totally reflected from an interface between a dielectric material block and a thin film layer of an analysis chip for supporting a sample, is detected with photodetector and as a two-dimensional image constituted of pixels arrayed in a beam width direction and an incidence angle direction, which are perpendicular to each other. An abnormal pixel row, which contains a pixel represented by abnormal pixel data, is extracted from among pixel rows, each of which extends in the incidence angle direction, in the array of the pixels constituting the two-dimensional image and in accordance with an output of the photodetector. A position of a dark line in the light beam, which has been totally reflected from the interface, is detected from the pixel data corresponding to the pixel rows other than the abnormal pixel row.

20 Claims, 6 Drawing Sheets

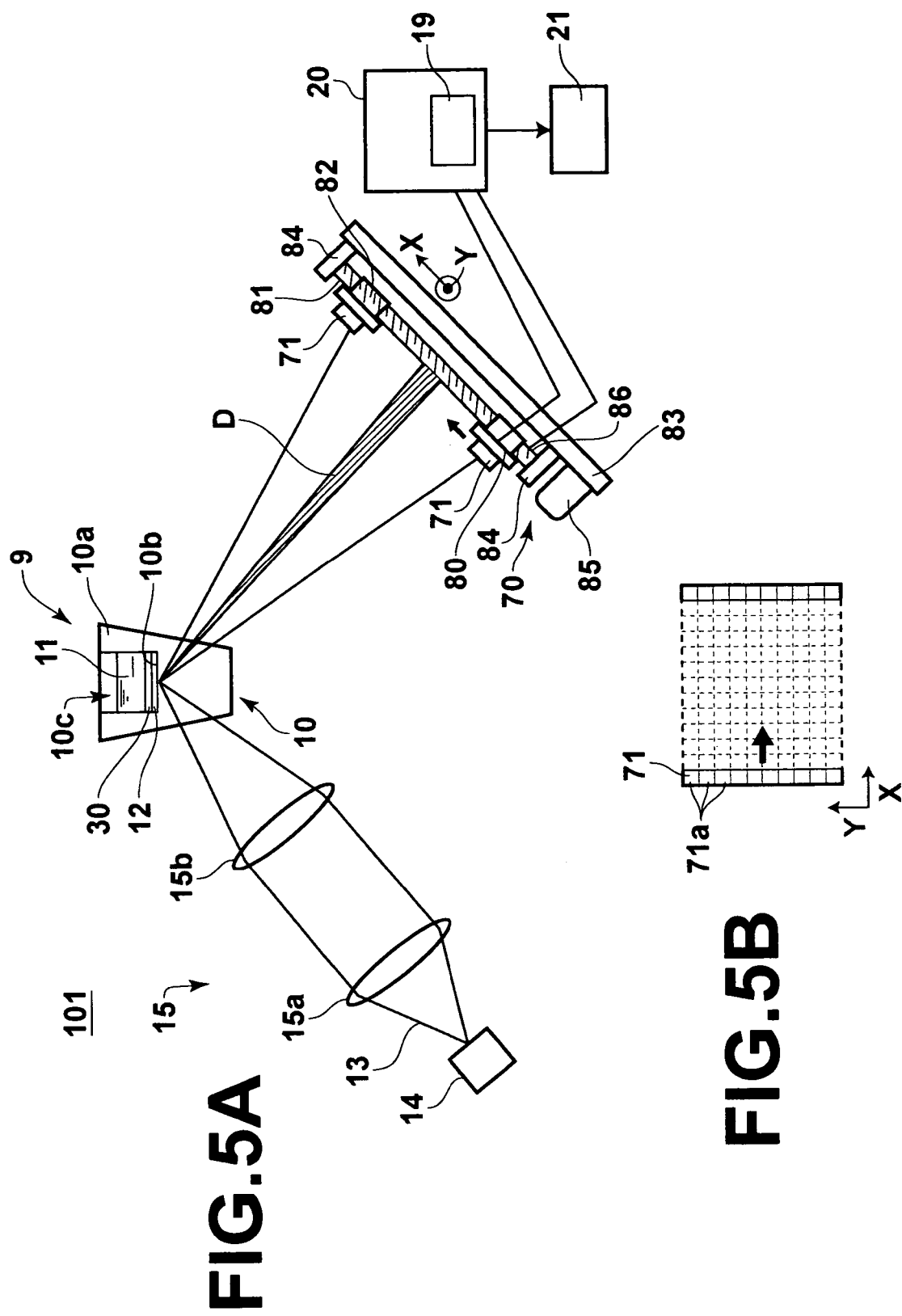

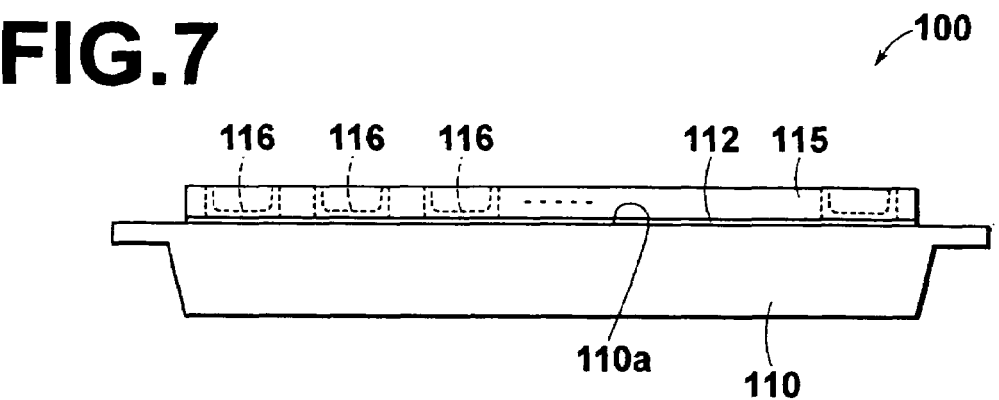
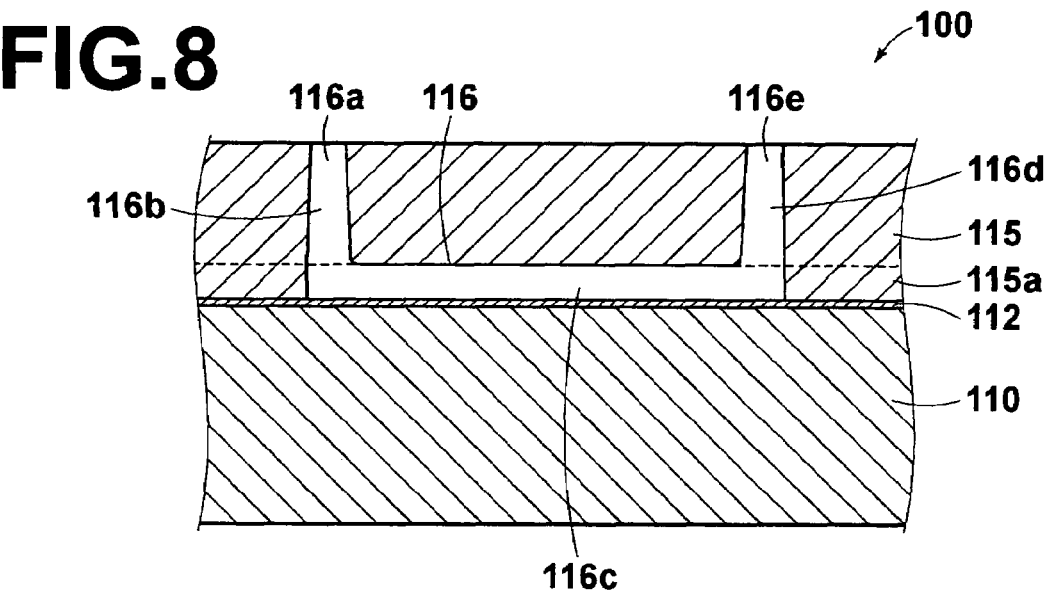

ized light.
ANALYSIS METHOD AND APPARATUS UTILIZING ATTENUATED TOTAL REFLECTION

BACKGROUND OF THE INVENTION

1. Field of the Invention

This invention relates to an analysis method and apparatus utilizing attenuated total reflection, such as a surface plasmon resonance analysis method and apparatus for making an analysis of a sample by the utilization of occurrence of surface plasmon.

2. Description of the Related Art

In metals, free electrons vibrate collectively, and a compression wave referred to as a plasma wave is thereby produced. The compression wave occurring on the metal surface and having been quantized is referred to as the surface plasmon.

Various surface plasmon analysis apparatuses for analyzing characteristics of a substance to be analyzed by the utilization of a phenomenon, in which the surface plasmon is excited by a light wave, have heretofore been proposed. As one of well known surface plasmon analysis apparatuses, a surface plasmon analysis apparatus utilizing a system referred to as the Kretschman arrangement may be mentioned. The surface plasmon analysis apparatus utilizing the system referred to as the Kretschman arrangement is described in, for example, Japanese Unexamined Patent Publication No. 6(1994)-167443.

Basically, the surface plasmon analysis apparatus utilizing the system referred to as the Kretschman arrangement comprises (i) a dielectric material block having, for example, a prism-like shape, (ii) a metal film, which is formed on one surface of the dielectric material block and is brought into contact with a substance to be analyzed, such as a liquid sample, (iii) a light source for producing a light beam, (iv) an optical system for irradiating the light beam to the dielectric material block at various different incidence angles such that a total reflection condition may be satisfied at an interface between the dielectric material block and the metal film, and (v) a photo detecting means for detecting the intensity of the light beam, which has been totally reflected from the interface described above, and thereby detecting the state of surface plasmon resonance, i.e. the state of attenuated total reflection.

In order for the various different incidence angles described above to be obtained, a light beam having a comparatively small beam diameter may be caused to impinge upon the aforesaid interface with the incidence angle being altered. Alternatively, a light beam having a comparatively large beam diameter may be caused to impinge upon the aforesaid interface in a state of converged light or in a state of a divergent light, such that the light beam may contain components, which impinge at various different incidence angles upon the interface. In the former case, the reflected light beam, which is reflected from the interface with its reflection angle altering in accordance with the alteration of the incidence angle of the incident light beam, may be detected with a small photodetector, which moves by being interlocked with the alteration of the reflection angle, or may be detected with an area sensor extending in the direction of alteration of the reflection angle. In the latter case, the light beam may be detected with an area sensor extending in a direction such that the area sensor is capable of receiving all of the light beam components having been reflected from the interface at various different reflection angles.

With the surface plasmon analysis apparatus having the constitution described above, in cases where the light beam impinges at a specific incidence angle, which is not smaller than the total reflection angle, upon the metal film, an evanescent wave having an electric field distribution occurs in the substance to be analyzed, which is in contact with the metal film, and the surface plasmon is excited by the evanescent wave and at the interface between the metal film and the substance to be analyzed. In cases where the wave vector of the evanescent wave coincides with the wave vector of the surface plasmon, and wave number matching is thus obtained, the evanescent wave and the surface plasmon resonate, and energy of the light transfers to the surface plasmon. As a result, the intensity of the reflected light beam, which is totally reflected from the interface between the dielectric material block and the metal film, becomes markedly low. Ordinarily, the lowering of the intensity of the reflected light beam is detected as a dark line by the photo detecting means described above. The resonance described above occurs only in cases where the incident light beam is P-polarized light. Therefore, it is necessary for the incident light beam to be set previously so as to impinge upon the aforesaid metal film as the P-polarized light.

In cases where the wave number of the surface plasmon is found from the incidence angle at which the attenuated total reflection (ATR) occurs, i.e. from an attenuated total reflection angle (ATR angle) $\theta_{SP}$, a dielectric constant of the substance to be analyzed is capable of being calculated. Specifically, the formula shown below obtains.

$$K_{SP}(\omega) = \frac{\omega}{c} \sqrt{\frac{\varepsilon_m(\omega)\varepsilon_s}{\varepsilon_m(\omega) + \varepsilon_s}}$$

wherein $K_{SP}$ represents the wave number of the surface plasmon, $\omega$ represents the angular frequency of the surface plasmon, c represents the light velocity in a vacuum, ∈m represents the dielectric constant of the metal, and ∈s represents the dielectric constant of the substance to be analyzed.

Specifically, in cases where the ATR angle $\theta_{SP}$, which is the incidence angle associated with the lowering of the intensity of the reflected light described above, is found, the dielectric constant ∈s of the substance to be analyzed is capable of being calculated. Therefore, the characteristics with regard to the refractive index of the substance to be analyzed are capable of being calculated.

Such that the ATR angle $\theta_{SP}$ may be measured accurately and with a wide dynamic range, a technique has been proposed, in which array-like photo detecting means is utilized in the aforesaid type of the surface plasmon analysis apparatus. (The proposed technique for utilizing the array-like photo detecting means is described in, for example, U.S. Pat. No. 6,577,396.) The array-like photo detecting means comprises a plurality of light receiving devices arrayed in a predetermined direction. The array-like photo detecting means is located in an orientation such that each of the light receiving devices is capable of receiving one of components of the light beam, which components have been totally reflected at various different reflection angles from the interface described above.

In such cases, the surface plasmon analysis apparatus is often provided with differentiation means for performing differentiation of signal components of a photo detection signal, each of which signal components is outputted from one of the light receiving devices of the aforesaid array-like photo detecting means, with respect to the array direction of the light receiving devices. Also, the characteristics with regard to the refractive index of the substance to be analyzed are calculated in accordance with differentiation values, which are outputted by the differentiation means.

As a similar analysis apparatus utilizing the attenuated total reflection (ATR), a leaky mode analysis apparatus has heretofore been known. (The leaky mode analysis apparatus is described in, for example, "Surface Refracto-sensor using Evanescent Waves: Principles and Instrumentations" Takayuki Okamura, Spectrum Researches, Vol. 47, No. 1, pp. 19-28, 1998.) Basically, the leaky mode analysis apparatus comprises (i) a dielectric material block having, for example, a prism-like shape, (ii) a cladding layer, which is formed on one surface of the dielectric material block, (iii) an optical waveguide layer, which is formed on the cladding layer and is brought into contact with a liquid sample, (iv) a light source for producing a light beam, (v) an optical system for irradiating the light beam to the dielectric material block at various different incidence angles such that a total reflection condition may be satisfied at an interface between the dielectric material block and the cladding layer, and (vi) a photo detecting means for detecting the intensity of the light beam, which has been totally reflected from the interface described above, and thereby detecting the state of excitation of a guided mode, i.e. the state of attenuated total reflection.

With the leaky mode analysis apparatus having the constitution described above, in cases where the light beam impinges at an incidence angle, which is not smaller than the total reflection angle, upon the cladding layer via the dielectric material block, only the light having a certain specific wave number, which light has impinged at a specific incidence angle upon the cladding layer, is propagated in the guided mode in the optical waveguide layer after passing through the cladding layer. In cases where the guided mode is thus excited, approximately all of the incident light is taken into the optical waveguide layer. Therefore, in such cases, the attenuated total reflection occurs, and the intensity of the light totally reflected from the aforesaid interface becomes markedly low. Also, the wave number of the guided optical wave depends upon the refractive index of the substance to be analyzed, which is located on the optical waveguide layer. Therefore, in cases where the aforesaid specific incidence angle, which is associated with the occurrence of the attenuated total reflection, is detected, the refractive index of the substance to be analyzed and characteristics of the substance to be analyzed with regard to the refractive index of the substance to be analyzed are capable of being analyzed.

In the leaky mode analysis apparatus, the array-like photo detecting means described above may be utilized in order to detect the position of the dark line occurring in the reflected light due to the attenuated total reflection. Also, the differentiation means described above is often utilized together with the array-like photo detecting means.

In the fields of pharmaceutical research, and the like, the surface plasmon analysis apparatus and the leaky mode analysis apparatus described above are often utilized for random screening for finding out a specific substance, which is capable of undergoing the binding with a desired sensing substance. In such cases, the sensing substance acting as the substance to be analyzed is fixed to the aforesaid thin film layer (the metal film in the cases of the surface plasmon analysis apparatus, or the combination of the cladding layer and the optical waveguide layer in the cases of the leaky mode analysis apparatus), and a liquid sample containing a test body in a solvent is introduced on the sensing substance. Also, at each of stages after the passage of predetermined periods of time, the aforesaid ATR angle $\theta_{SP}$ is measured.

In cases where the test body contained in the liquid sample is a substance capable of undergoing the binding with the sensing substance, the refractive index of the sensing substance alters with the passage of time. Therefore, the aforesaid ATR angle $\theta_{SP}$ is measured at each of stages after the passage of predetermined periods of time, and a judgment is made as to whether an alteration of the ATR angle $\theta_{SP}$ has been or has not been occurred. In this manner, the state of the binding of the test body with the sensing substance is capable of being detected, and a judgment is capable of being made in accordance with the result of the detection and as to whether the test body is or is not the specific substance capable of undergoing the binding with the sensing substance. Examples of the combinations of the specific substances and the sensing substances include the combination of an antigen and an antibody and the combination of an antibody and a different antibody. Specifically, for example, a rabbit anti-human IgG antibody may be fixed as the sensing substance to the surface of the thin film layer, and a human IgG antibody may be employed as the specific substance.

In order for the state of the binding of the test body with the sensing substance to be detected, the ATR angle $\theta_{SP}$ itself need not necessarily be detected. Alternatively, for example, the liquid sample may be introduced on the sensing substance, and thereafter the quantity of the alteration of the ATR angle $\theta_{SP}$ may be measured. Also, the state of the binding of the test body with the sensing substance may be detected in accordance with the quantity of the alteration of the ATR angle $\theta_{SP}$. In cases where the array-like photo detecting means and the differentiation means described above are utilized in the analysis apparatus utilizing attenuated total reflection, since the quantity of the alteration of the differentiation value reflects the quantity of the alteration of the ATR angle $\theta_{SP}$, the state of the binding of the test body with the sensing substance is capable of being detected in accordance with the quantity of the alteration of the differentiation value.

In the analysis method and apparatus utilizing attenuated total reflection as described above, a cup-shaped or laboratory dish-shaped analysis chip, in which the sensing substance has been fixed to the thin film layer having been formed previously on a bottom surface, is prepared. Also, the liquid sample containing the test body in the solvent is introduced into the analysis chip, and the quantity of the alteration of the ATR angle $\theta_{SP}$ is measured.

In cases where the liquid sample is introduced into the analysis chip, and the sensing substance and the test body are bound to each other, the refractive index of the sensing substance alters, and the ATR angle $\theta_{SP}$ alters. Therefore, at the time at which a predetermined period of time has elapsed after the measurement has been begun, the quantity of the alteration of the ATR angle $\theta_{SP}$ occurring after the measurement has been begun may be calculated. In this manner, a judgment is capable of being made as to whether the test body is or is not a substance capable of undergoing the binding with the sensing substance. Also, in cases where it has been judged that the test body is a substance capable of undergoing the binding with the sensing substance, the state of the binding of the test body with the sensing substance, or the like, is capable of being analyzed.

As described above, the array-like photo detecting means, which is described in, for example, U.S. Pat. No. 6,577,396 and which is utilized for the enhancement of sensitivity comprises the plurality of the light receiving devices arrayed in the predetermined direction. The array-like photo detecting means is located in the orientation such that each of the light receiving devices is capable of receiving one of the components of the light beam, which components have been totally reflected at various different reflection angles from the interface described above. The components of the light beam, which components are taken in a beam width direction perpendicular to the reflection angle direction and with respect to each of the various different reflection angles, are received by one light receiving device. Therefore, the output obtained from each of the light receiving devices contains all of the information with respect to the beam width direction. However, in cases where the surface of the thin film layer of the analysis chip is not uniform, in cases where the sensing substance is not uniform, or in cases where staining occurs at part of the optical system, the problems often occur in that part of the dark line is deformed (for example, part of the dark line becomes dull). Therefore, with the conventional analysis apparatus provided with the array-like photo detecting means, in cases where part of the dark line is deformed due to defects, such as non-uniformity, staining, and the like, of part of the analysis chip or part of the optical system, a measurement result containing adverse effects of the deformation of part of the dark line is obtained. Accordingly, with the conventional analysis apparatus provided with the array-like photo detecting means, there is the possibility that the detection sensitivity will become low.

SUMMARY OF THE INVENTION

The primary object of the present invention is to provide an analysis method utilizing attenuated total reflection, wherein lowering of a signal detection sensitivity due to non-uniformity, staining, or the like, of part of an analysis chip, part of an optical system, or the like, is capable of being suppressed.

Another object of the present invention is to provide an apparatus for carrying out the analysis method utilizing attenuated total reflection.

The present invention provides a first analysis method utilizing attenuated total reflection, comprising the steps of:

i) preparing an analysis chip, which is provided with a dielectric material block transparent with respect to a light beam having been produced by a light source, a thin film layer formed on one surface of the dielectric material block, and a sample support section for supporting a sample on a surface of the thin film layer, ii) irradiating the light beam, which has been produced by the light source, to the dielectric material block so as to have a predetermined beam width with respect to an interface between the dielectric material block and the thin film layer and at various different incidence angles such that a total reflection condition is satisfied at the interface between the dielectric material block and the thin film layer, and iii) measuring a position of a dark line in the light beam, which has been totally reflected from the interface between the dielectric material block and the thin film layer, wherein the measurement of the position of the dark line is performed with a process comprising:

a) detecting an image of the light beam, which has been totally reflected from the interface between the dielectric material block and the thin film layer, with photo detecting means and as a two-dimensional image constituted of a plurality of pixels arrayed in two-dimensional directions composed of a beam width direction and an incidence angle direction, which are perpendicular to each other, b) extracting an abnormal pixel row, which contains a pixel represented by abnormal pixel data, from among pixel rows, each of which extends in the incidence angle direction, in the array of the pixels constituting the two-dimensional image and in accordance with an output obtained from the photo detecting means, which has detected the two-dimensional image with respect to the sample having been supported by the analysis chip, and c) calculating the position of the dark line with respect to the sample and in accordance with the pixel data corresponding to the pixel rows other than the abnormal pixel row, which has been extracted.

The present invention also provides a second analysis method utilizing attenuated total reflection, comprising the steps of:

i) preparing an analysis chip, which is provided with a dielectric material block transparent with respect to a light beam having been produced by a light source, a thin film layer formed on one surface of the dielectric material block, and a sample support section for supporting a sample on a surface of the thin film layer, ii) irradiating the light beam, which has been produced by the light source, to the dielectric material block so as to have a predetermined beam width with respect to an interface between the dielectric material block and the thin film layer and at various different incidence angles such that a total reflection condition is satisfied at the interface between the dielectric material block and the thin film layer, and iii) measuring a position of a dark line in the light beam, which has been totally reflected from the interface between the dielectric material block and the thin film layer, wherein the measurement of the position of the dark line is performed with a process comprising:

a) detecting an image of the light beam, which has been totally reflected from the interface between the dielectric material block and the thin film layer, with photo detecting means and as a two-dimensional image constituted of a plurality of pixels arrayed in two-dimensional directions composed of a beam width direction and an incidence angle direction, which are perpendicular to each other, b) extracting an abnormal pixel row, which contains a pixel represented by abnormal pixel data, from among pixel rows, each of which extends in the incidence angle direction, in the array of the pixels constituting the two-dimensional image and in accordance with an output obtained from the photo detecting means, which has detected the two-dimensional image with respect to a reference sample having been supported by the analysis chip, and c) calculating the position of the dark line with respect to the reference sample and in accordance with the pixel data corresponding to the pixel rows other than the abnormal pixel row, which has been extracted.

The term "abnormal pixel data" as used herein means the pixel data occurring due to, for example, non-uniformity of the thin film layer of the analysis chip, or the like, or staining of an optical system for irradiating the light beam, which has been produced by the light source, to the dielectric material block.

In order for the position of the dark line to be measured, the ATR angle $\theta_{SP}$, which uniquely corresponds to the refractive index of the sample to be analyzed, may be calculated. Alternatively, a value with regard to the position of the dark line, such as the quantity of the alteration of the ATR angle $\theta_{SP}$, which quantity corresponds to a difference in refractive index of the sample to be analyzed, may be measured.

Each of the first and second analysis methods utilizing attenuated total reflection in accordance with the present invention may be modified such that the extraction of the abnormal pixel row, which contains the pixel represented by the abnormal pixel data, is performed with a process for:

forming an output distribution profile of each of pixel columns, each of which extends in the beam width direction, in the array of the pixels constituting the two-dimensional image and in accordance with the output obtained from the photo detecting means, comparing the output distribution profile and a normal distribution with each other, detecting a pixel associated with a rate of deviation from the normal distribution, which rate of deviation is higher than a predetermined value, and extracting a pixel row extending in the incidence angle direction, which pixel row contains the thus detected pixel, as the abnormal pixel row.

Also, the second analysis method utilizing attenuated total reflection in accordance with the present invention may be modified such that the extraction of the abnormal pixel row, which contains the pixel represented by the abnormal pixel data, is performed with a process for:

obtaining the output from the photo detecting means and with respect to each of a plurality of reference samples, differences in refractive index among the plurality of the reference samples being known previously, calculating an alteration of the position of the dark line with respect to the incidence angle direction, which alteration occurs in each of the pixel rows extending in the incidence angle direction, detecting a pixel row associated with the alteration of the position of the dark line with respect to the incidence angle direction, which alteration varies from an ideal alteration obtained from the differences in refractive index among the plurality of the reference samples, and extracting the thus detected pixel row as the abnormal pixel row.

Further, each of the first and second analysis methods utilizing attenuated total reflection in accordance with the present invention may be modified such that the photo detecting means comprises a plurality of light receiving devices, which are arrayed in the two-dimensional directions composed of the beam width direction and the incidence angle direction.

Alternatively, each of the first and second analysis methods utilizing attenuated total reflection in accordance with the present invention may be modified such that the photo detecting means comprises a light receiving section, which is provided with a plurality of light receiving devices arrayed in the beam width direction, and a movement section for moving the light receiving section in the incidence angle direction.

Each of the first and second analysis methods utilizing attenuated total reflection in accordance with the present invention may be constituted as a surface plasmon resonance analysis method, wherein a metal film is utilized as the thin film layer. Also, each of the first and second analysis methods utilizing attenuated total reflection in accordance with the present invention may be constituted as a leaky mode analysis method, wherein a combination of a cladding layer, which is formed on one surface of the dielectric material block, and an optical waveguide layer, which is formed on the cladding layer, is utilized as the thin film layer.

The present invention further provides a first analysis apparatus utilizing attenuated total reflection, comprising:

i) a light source for producing a light beam, ii) an analysis chip, which is provided with a dielectric material block transparent with respect to the light beam having been produced by the light source, a thin film layer formed on one surface of the dielectric material block, and a sample support section for supporting a sample on a surface of the thin film layer, iii) a light beam irradiating optical system for irradiating the light beam, which has been produced by the light source, to the dielectric material block so as to have a predetermined beam width with respect to an interface between the dielectric material block and the thin film layer and at various different incidence angles such that a total reflection condition is satisfied at the interface between the dielectric material block and the thin film layer, and iv) measurement means for measuring a position of a dark line in the light beam, which has been totally reflected from the interface between the dielectric material block and the thin film layer, wherein the measurement means is provided with:

a) photo detecting means for detecting an image of the light beam, which has been totally reflected from the interface between the dielectric material block and the thin film layer, as a two-dimensional image constituted of a plurality of pixels arrayed in two-dimensional directions composed of a beam width direction and an incidence angle direction, which are perpendicular to each other, and b) extraction means for extracting an abnormal pixel row, which contains a pixel represented by abnormal pixel data, from among pixel rows, each of which extends in the incidence angle direction, in the array of the pixels constituting the two-dimensional image and in accordance with an output obtained from the photo detecting means, which has detected the two-dimensional image with respect to the sample having been supported by the analysis chip, and the measurement means calculates the position of the dark line with respect to the sample and in accordance with the pixel data corresponding to the pixel rows other than the abnormal pixel row, which has been extracted by the extraction means.

The present invention still further provides a second analysis apparatus utilizing attenuated total reflection, comprising:

i) a light source for producing a light beam, ii) an analysis chip, which is provided with a dielectric material block transparent with respect to the light beam having been produced by the light source, a thin film layer formed on one surface of the dielectric material block, and a sample support section for supporting a sample on a surface of the thin film layer, iii) a light beam irradiating optical system for irradiating the light beam, which has been produced by the light source, to the dielectric material block so as to have a predetermined beam width with respect to an interface between the dielectric material block and the thin film layer and at various different incidence angles such that a total reflection condition is satisfied at the interface between the dielectric material block and the thin film layer, and iv) measurement means for measuring a position of a dark line in the light beam, which has been totally reflected from the interface between the dielectric material block and the thin film layer, wherein the measurement means is provided with:

a) photo detecting means for detecting an image of the light beam, which has been totally reflected from the interface between the dielectric material block and the thin film layer, as a two-dimensional image constituted of a plurality of pixels arrayed in two-dimensional directions composed of a beam width direction and an incidence angle direction, which are perpendicular to each other, and b) extraction means for extracting an abnormal pixel row, which contains a pixel represented by abnormal pixel data, from among pixel rows, each of which extends in the incidence angle direction, in the array of the pixels constituting the two-dimensional image and in accordance with an output obtained from the photo detecting means, which has detected the two-dimensional image with respect to a reference sample having been supported by the analysis chip, and the measurement means calculates the position of the dark line with respect to the reference sample and in accordance with the pixel data corresponding to the pixel rows other than the abnormal pixel row, which has been extracted by the extraction means.

Each of the first and second analysis apparatuses utilizing attenuated total reflection in accordance with the present invention may be modified such that the extraction means performs a process for:

forming an output distribution profile of each of pixel columns, each of which extends in the beam width direction, in the array of the pixels constituting the two-dimensional image and in accordance with the output obtained from the photo detecting means, comparing the output distribution profile and a perpendicular distribution with each other, detecting a pixel associated with a rate of deviation from the normal distribution, which rate of deviation is higher than a predetermined value, and extracting a pixel row extending in the incidence angle direction, which pixel row contains the thus detected pixel, as the abnormal pixel row.

Also, the second analysis apparatus utilizing attenuated total reflection in accordance with the present invention may be modified such that the extraction means performs a process for:

obtaining the output from the photo detecting means and with respect to each of a plurality of reference samples, differences in refractive index among the plurality of the reference samples being known previously, calculating an alteration of the position of the dark line with respect to the incidence angle direction, which alteration occurs in each of the pixel rows extending in the incidence angle direction, detecting a pixel row associated with the alteration of the position of the dark line with respect to the incidence angle direction, which alteration varies from an ideal alteration obtained from the differences in refractive index among the plurality of the reference samples, and extracting the thus detected pixel row as the abnormal pixel row.

Further, each of the first and second analysis apparatuses utilizing attenuated total reflection in accordance with the present invention may be modified such that the photo detecting means comprises a plurality of light receiving devices, which are arrayed in the two-dimensional directions composed of the beam width direction and the incidence angle direction.

Alternatively, each of the first and second analysis apparatuses utilizing attenuated total reflection in accordance with the present invention may be modified such that the photo detecting means comprises a light receiving section, which is provided with a plurality of light receiving devices arrayed in the beam width direction, and a movement section for moving the light receiving section in the incidence angle direction.

Each of the first and second analysis apparatuses utilizing attenuated total reflection in accordance with the present invention may be constituted as a surface plasmon resonance analysis apparatus, wherein a metal film is utilized as the thin film layer. Also, each of the first and second analysis apparatuses utilizing attenuated total reflection in accordance with the present invention may be constituted as a leaky mode analysis apparatus, wherein a combination of a cladding layer, which is formed on one surface of the dielectric material block, and an optical waveguide layer, which is formed on the cladding layer, is utilized as the thin film layer.

In the first analysis method and apparatus utilizing attenuated total reflection and the second analysis method and apparatus utilizing attenuated total reflection in accordance with the present invention, as the technique for detecting the position of the dark line, besides the difference technique, a centroid algorithm technique may be employed. The centroid algorithm technique is described in, for example, "Surface Plasmon Resonance: Instrumental Resolution Using Photo Diode Array," Measurement Science and Technology, 11 (2000), pp. 1630-1638.

With the first analysis method and apparatus utilizing attenuated total reflection in accordance with the present invention, the image of the light beam, which has been totally reflected from the interface between the dielectric material block and the thin film layer, is detected with the photo detecting means and as the two-dimensional image constituted of the plurality of the pixels arrayed in the two-dimensional directions composed of the beam width direction and the incidence angle direction, which are perpendicular to each other. Also, the abnormal pixel row, which contains the pixel represented by the abnormal pixel data, is extracted from among the pixel rows, each of which extends in the incidence angle direction, in the array of the pixels constituting the two-dimensional image and in accordance with the output obtained from the photo detecting means, which has detected the two-dimensional image with respect to the sample having been supported by the analysis chip. Further, the position of the dark line is calculated with respect to the sample and in accordance with the pixel data corresponding to the pixel rows other than the abnormal pixel row, which has been extracted. Therefore, with the first analysis method and apparatus utilizing attenuated total reflection in accordance with the present invention, in cases where the dark line is deformed due to non-uniformity, and the like, of part of the optical path, a measurement result free from adverse effects of the deformation of the dark line is capable of being obtained.

With the second analysis method and apparatus utilizing attenuated total reflection in accordance with the present invention, the image of the light beam, which has been totally reflected from the interface between the dielectric material block and the thin film layer, is detected with the photo detecting means and as the two-dimensional image constituted of the plurality of the pixels arrayed in the two-dimensional directions composed of the beam width direction and the incidence angle direction, which are perpendicular to each other. Also, the abnormal pixel row, which contains the pixel represented by the abnormal pixel data, is extracted from among the pixel rows, each of which extends in the incidence angle direction, in the array of the pixels constituting the two-dimensional image and in accordance with the output obtained from the photo detecting means, which has detected the two-dimensional image with respect to the reference sample having been supported by the analysis chip. Further, the position of the dark line is calculated with respect to the reference sample and in accordance with the pixel data corresponding to the pixel rows other than the abnormal pixel row, which has been extracted. Therefore, with the second analysis method and apparatus utilizing attenuated total reflection in accordance with the present invention, in cases where the dark line is deformed due to non-uniformity, and the like, of part of the optical path, a measurement result free from adverse effects of the deformation of the dark line is capable of being obtained.

BRIEF DESCRIPTION OF THE DRAWINGS

FIG. 3a is a graph showing intensity distribution profiles of pixel columns in the image shown in FIG. 3A, which pixel columns stand side by side with respect to the incidence angle direction and along which pixel columns a dark line has been detected, the intensity distribution profiles being taken in the beam width direction, FIG. 3b is a graph showing intensity distribution profiles of pixel columns in the image shown in FIG. 3B, which pixel columns stand side by side with respect to the incidence angle direction and along which pixel columns a dark line has been detected, the intensity distribution profiles being taken in the beam width direction, FIG. 5A is a schematic side view showing a second embodiment of the analysis apparatus utilizing attenuated total reflection in accordance with the present invention, which is constituted as a surface plasmon resonance analysis apparatus, FIG. 5B is an explanatory plan view showing photo detecting means utilized in the surface plasmon resonance analysis apparatus of FIG. 5A, FIG. 7 is a front view showing an example of a sensor unit, and FIG. 8 is a sectional view showing part of the sensor unit of FIG. 7.

DESCRIPTION OF THE PREFERRED EMBODIMENTS

The present invention will hereinbelow be described in further detail with reference to the accompanying drawings.

Figures 1A, 1B:
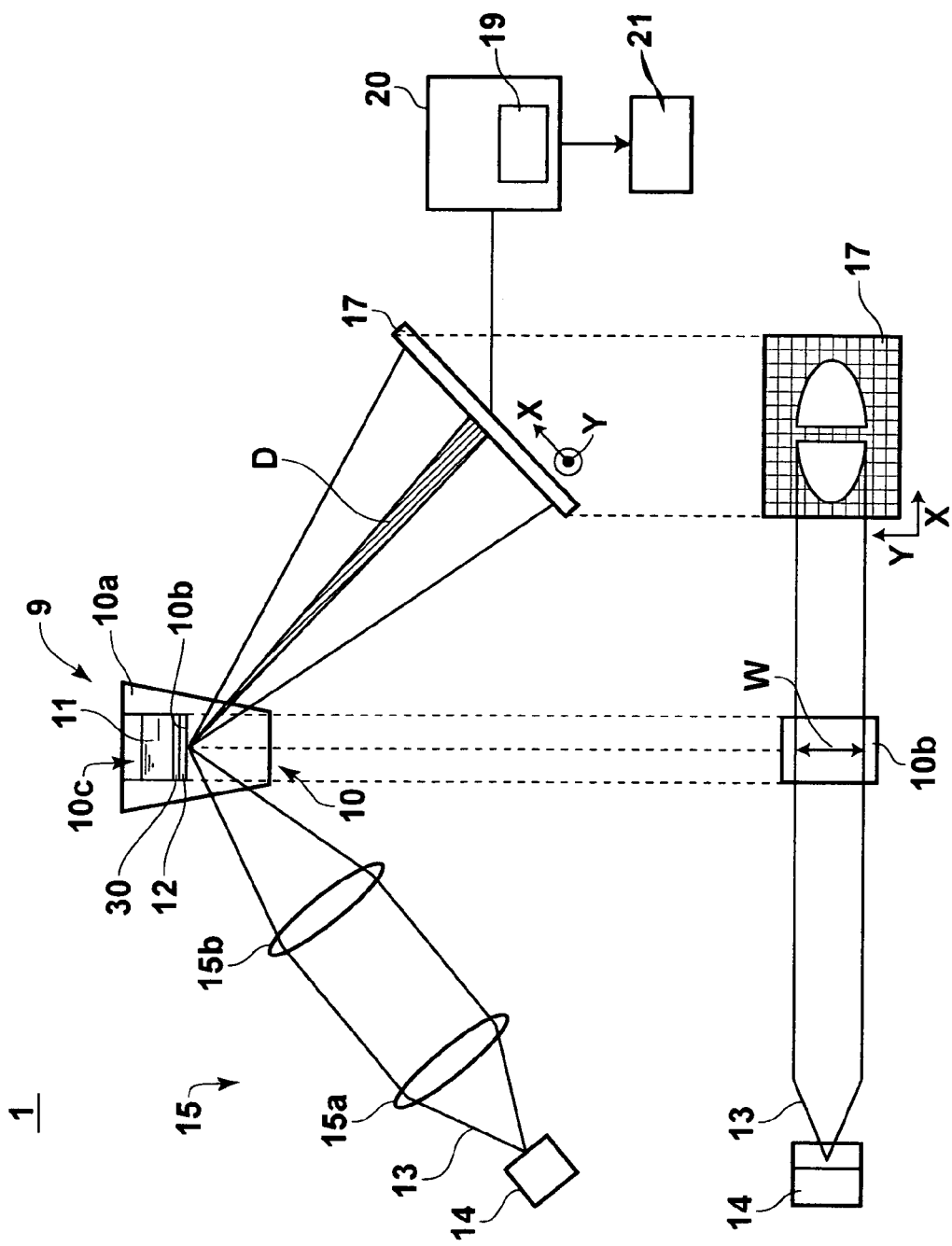
FIG. 1A is a schematic side view showing a first embodiment of the analysis apparatus utilizing attenuated total reflection in accordance with the present invention, which is constituted as a surface plasmon resonance analysis apparatus.
FIG. 1B is an explanatory plan view showing an optical path in the surface plasmon resonance analysis apparatus of FIG. 1A and an image formed by a light beam on a light receiving surface of photo detecting means.

FIG. 1A is a schematic side view showing a first embodiment of the analysis apparatus utilizing attenuated total reflection in accordance with the present invention, which is constituted as a surface plasmon resonance analysis apparatus. FIG. 1B is an explanatory plan view showing an optical path in the surface plasmon resonance analysis apparatus of FIG. 1A and an image formed by a light beam on a light receiving surface of photo detecting means.

With reference to FIG. 1A, a surface plasmon resonance analysis apparatus 1, which is the first embodiment of the analysis apparatus utilizing attenuated total reflection in accordance with the present invention, comprises an analysis chip 9. The surface plasmon resonance analysis apparatus 1 also comprises a laser beam source 14, which acts as a light source for producing a laser beam 13. The surface plasmon resonance analysis apparatus 1 further comprises a laser beam irradiating optical system 15 for irradiating the laser beam 13 to the analysis chip 9. The surface plasmon resonance analysis apparatus 1 still further comprises photo detecting means 17 for receiving the laser beam 13, which has been reflected from the analysis chip 9. The surface plasmon resonance analysis apparatus 1 also comprises a signal processing section 20 provided with extraction means 19, which will be described later. The signal processing section 20 receives an output from the photo detecting means 17 and calculates a position of a dark line in the laser beam 13, which has been reflected from the analysis chip 9. The surface plasmon resonance analysis apparatus 1 further comprises displaying means 21, which is connected to the signal processing section 20.

The analysis chip 9 comprises a dielectric material block 10 having a truncated quadrangular pyramid-like shape, i.e. a shape obtained by truncating a region containing a vertex, at which four edge lines of a quadrangular pyramid gather. A recess 10c acting as the sample support section for accommodating a liquid sample 11 is formed at the bottom region of the truncated quadrangular pyramid-like shape. The analysis chip 9 also comprises a metal film 12, which acts as the thin film layer and is made from gold, silver, copper, aluminum, or the like. The metal film 12 is formed on a bottom surface of the recess 10c of the dielectric material block 10. By way of example, the dielectric material block 10 may be made from a transparent resin. A sensing medium 30, which will be described later, may be located on the metal film 12.

The laser beam irradiating optical system 15 comprises a collimator lens 15a for collimating the laser beam 13, which has been radiated out from the laser beam source 14. The laser beam irradiating optical system 15 also comprises a converging lens 15b for converging the collimated laser beam 13 toward an interface 10b between the dielectric material block 10 and the metal film 12.

The laser beam 13 is converged by the converging lens 15b in the manner described above. Therefore, the laser beam 13 contains laser beam components, which impinge at various different incidence angles θ upon the interface 10b. The incidence angles θ upon the interface 10b are set to be not smaller than the total reflection angle. Therefore, the laser beam 13, which has been totally reflected from the interface 10b, contains the laser beam components, which have been totally reflected at various different reflection angles. Also, as illustrated in FIG. 1B, the laser beam 13 impinges upon the interface 10b so as to have a predetermined beam width W.

The laser beam 13 is irradiated so as to impinge as P-polarized light upon the interface 10b. In order for the laser beam 13 to impinge as the P-polarized light upon the interface 10b, the laser beam source 14 may be located such that the direction of polarization of the laser beam 13 may coincide with the predetermined direction described above. Alternatively, the direction of polarization of the laser beam 13 may be controlled with a wave plate such that the laser beam 13 may impinge as the P-polarized light upon the interface 10b.

The photo detecting means 17 is constituted of a CCD image sensor, which comprises a plurality of pixels arrayed in two-dimensional directions. The plurality of the pixels are arrayed in the two-dimensional directions composed of a direction (i.e., an incidence angle direction) X, which is indicated by the arrow X and is approximately parallel to the plane of the sheet of FIG. 1A, and a beam width direction Y, which is indicated by the arrow Y and is perpendicular to the incidence angle direction X. The CCD image sensor 17 is located such that a light receiving surface of the CCD image sensor 17 may be approximately perpendicular to the direction of propagation of the laser beam 13. Specifically, the CCD image sensor 17 is located such that each of the laser beam components of the laser beam 13, which laser beam components have been totally reflected at various different reflection angles from the interface 10b, may be received by one of the different pixels of the CCD image sensor 17, which pixels are arrayed in the incidence angle direction X, and such that each of the laser beam components of the laser beam 13, which laser beam components are taken in the beam width direction Y, may be received by one of the different pixels of the CCD image sensor 17, which pixels are arrayed in the beam width direction Y.

How an analysis of a sample is made with the surface plasmon resonance analysis apparatus 1 having the constitution described above will be described hereinbelow.

Specifically, how the analysis of the sample is made in cases where the sensing medium 30, which is capable of undergoing the binding with a specific substance, is fixed onto the metal film 12, and in cases where a state of binding of a substance to be analyzed, which is contained the liquid sample 11, and the sensing medium 30 with each other is to be measured will be described hereinbelow. By way of example, as the combination of the sensing medium 30 and the specific substance, a combination of an antigen and an antibody may be employed. Ordinarily, the sensing medium 30 is referred to as the ligand, and the substance to be analyzed, which is contained in the liquid sample 11, is referred to as the analyte.

As illustrated in FIG. 1A, the laser beam 13, which has been produced by the laser beam source 14, passes through the laser beam irradiating optical system 15 and is converged onto the interface 10b between the dielectric material block 10 and the metal film 12.

The laser beam 13, which has been converged onto the interface 10b and has been totally reflected from the interface 10b, is detected by the CCD image sensor 17. The CCD image sensor 17 outputs signal components, which have respectively been detected by the pixels of the CCD image sensor 17 and which represent the distribution of intensities of the laser beam 13.

A laser beam component of the laser beam 13, which laser beam component has impinged at a specific angle $\theta_{SP}$ upon the interface 10b, excites surface plasmon to occur at the interface between the metal film 12 and the substance, which is in contact with the metal film 12. Therefore, as the laser beam component described above, the reflected light intensity becomes markedly low. Specifically, the specific angle θSP constitutes the ATR angle $\theta_{SP}$. At the ATR angle $\theta_{SP}$, the reflected light intensity takes a minimum value. As indicated by D in FIG. 1A, the region, in which the reflected light intensity becomes markedly low, is found as a dark line in the laser beam 13, which has been totally reflected from the interface 10b.

Figure 2A:
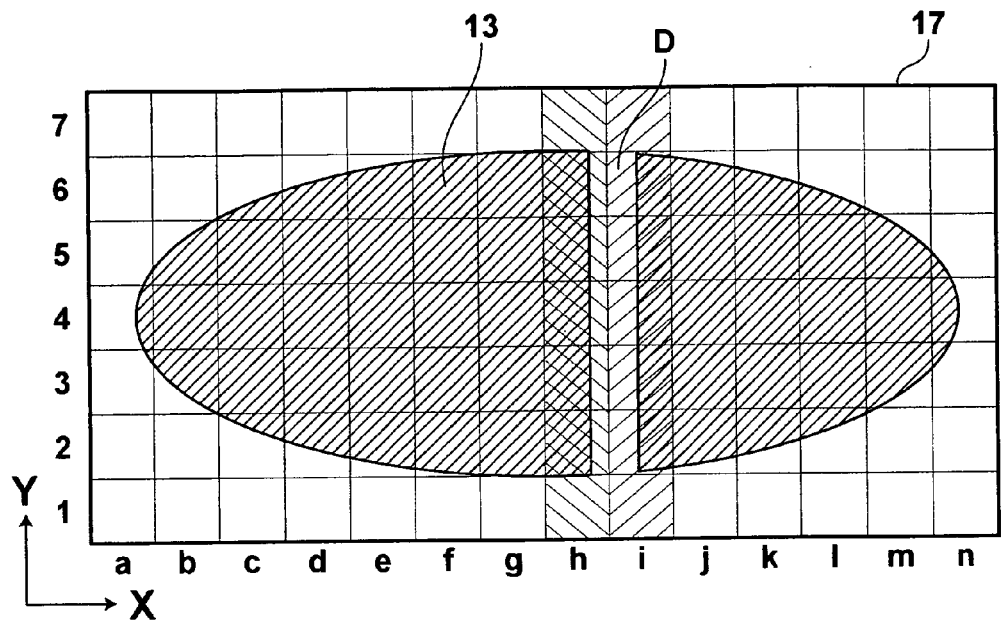
FIG. 2A is an explanatory view showing the image formed by the light beam on the light receiving surface of the photo detecting means.
Figure 2B:
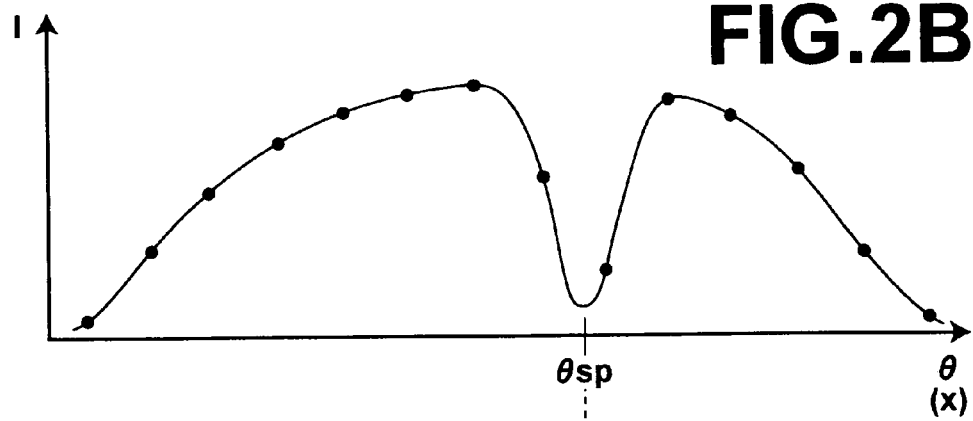
FIG. 2B is a graph showing an intensity distribution profile taken in an incidence angle direction, which profile is obtained from an output of the photo detecting means.
Figure 2C:
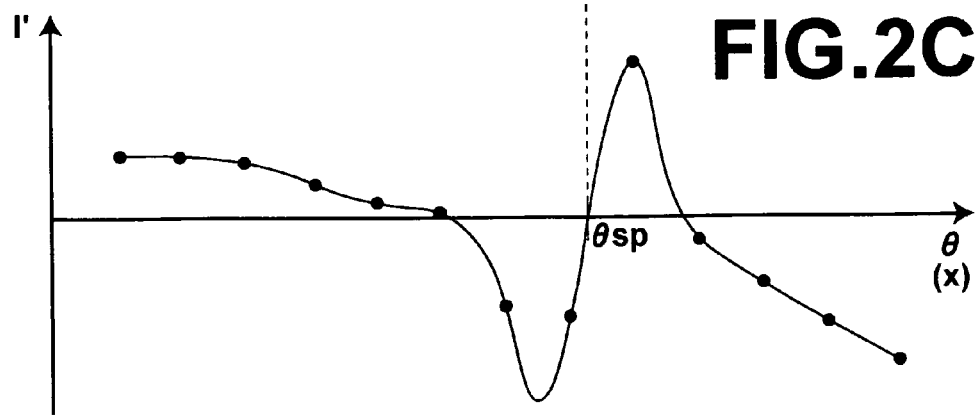
FIG. 2C is a graph showing a difference profile taken in the incidence angle direction, which profile represents differences among pixel columns adjacent to one another with respect to the incidence angle direction.

FIG. 2A is an explanatory view showing the image formed by the laser beam 13, which has been totally reflected from the interface 10b, on the light receiving surface of the CCD image sensor 17. FIG. 2B is a graph showing an intensity distribution profile taken in the incidence angle direction X, which profile is obtained from the output of the CCD image sensor 17. FIG. 2C is a graph showing a difference profile taken in the incidence angle direction X, which profile represents differences among pixel columns adjacent to one another with respect to the incidence angle direction X in the CCD image sensor 17.

In this embodiment, as illustrated in FIG. 2A, the CCD image sensor 17 comprises the light receiving devices arrayed along a plurality of pixel columns Xa, Xb, Xc, ..., Xn, which stand side by side with respect to the incidence angle direction X, and along a plurality of pixel rows Y1, Y2, Y3, ..., Y7, which stand side by side with respect to the beam width direction Y. However, the number of the light receiving devices (i.e., the number of the pixels) of the CCD image sensor 17 may be set arbitrarily. As described above, the incidence angle direction X corresponds to the incidence angle direction of the laser beam 13 upon the interface 10b, and the beam width direction Y corresponds to the beam width direction of the laser beam 13. The position taken in the incidence angle direction X uniquely corresponds to the incidence angle θ. The pixel columns, each of which extends in the beam width direction Y, are herein referred to as the pixel columns X. The pixel columns, each of which extends in the beam width direction Y and at each of positions a, b, c, ... n taken with respect to the incidence angle direction X, are herein referred to as the pixel columns Xa, Xb, Xc, ..., Xn. Also, the pixel rows, each of which extends in the incidence angle direction X, are herein referred to as the pixel rows Y. The pixel rows, each of which extends in the incidence angle direction X and at each of positions 1, 2, 3, ... 7 taken with respect to the beam width direction Y, are herein referred to as the pixel rows Y1, Y2, Y3, ..., Y7.

The dark line D in the laser beam 13 impinges as an image, which is illustrated in, for example, FIG. 2A, upon the light receiving surface of the CCD image sensor 17. With the surface plasmon resonance analysis apparatus 1, an alteration (a shift) of the position of the dark line D, which occurs in the laser beam 13, is detected, and the analysis of the sample is made in accordance with the results of the detection of the alteration of the position of the dark line D.

With respect to each of the pixel columns Xa, Xb, Xc, ..., Xn, the outputs having been obtained from the light receiving devices, which are arrayed in the beam width direction Y, are added together. For example, the output (i.e., the intensity) I obtained from the pixel column Xh is represented by the sum of the outputs obtained from the plurality of the light receiving devices, which are hatched with the lines inclined downwardly toward the right in FIG. 2A. Also, the intensity distribution profile of the laser beam 13 taken in the incidence angle direction X, which profile is obtained from the output of each of the pixel columns Xa, Xb, Xc, Xn, takes on the form illustrated in FIG. 2B. Each of the light receiving devices will hereinbelow be represented by the pixel $P_{XY}$. The lower suffix XY of $P_{XY}$ represents the position in the two-dimensional image. For example, the pixel, which is located at the pixel column a and the pixel row 1, is represented by $P_{a1}$.

As illustrated in FIG. 2C, the signal processing section 20 calculates the difference profile taken in the incidence angle direction X, which profile represents differences in outputs among the pixel columns Xa, Xb, Xc, ..., Xn adjacent to one another with respect to the incidence angle direction X. Also, the signal processing section 20 detects the adjacent pixel columns Xh and Xi, which contain the dark line D. Specifically, the signal processing section 20 generates an SPR signal, which represents the difference value between the pixel data of the adjacent pixel columns containing the dark line D. Also, the signal processing section 20 detects the alteration of the position of the dark line in accordance with an alteration of the SPR signal. The pixel data corresponds to the output (the voltage) obtained from the light receiving device. In cases where the state of the binding of the substance to be analyzed and the sensing substance with each other alters, the refractive index of the substance, which is in contact with the metal film 12, alters. As a result, the position of the dark line D alters. Therefore, the difference value described above alters. Accordingly, in cases where the difference value is measured successively or intermittently with the passage of time, the alteration of the state of the binding of the substance to be analyzed and the sensing substance with each other is capable of being measured.

In the foregoing, as an aid in facilitating the explanation, it is assumed that the output obtained from each of the pixel columns Xa, Xb, Xc, ..., Xn is the sum of the outputs obtained from all of the light receiving devices of each pixel column, which light receiving devices are arrayed in the beam width direction Y. However, as described above, for example, in cases where a non-uniform part is present on the optical path (e.g., in cases where the interface 10b has anon-uniform part, or in cases where part of the optical system is stained), abnormality occurs with the profile of the dark line D. In such cases, the problems occur in that the outputs obtained from the light receiving devices contain adverse effects of the abnormality occurring with the profile of the dark line D. In order for the problems described above to be eliminated, the signal processing section 20 makes a judgment as to whether the abnormality has or has not occurred. In cases where it has been judged that the abnormality has occurred, the extraction means 19 extracts a pixel corresponding to the abnormal part. Also, such that the output from the pixel corresponding to the abnormal part may not be used at the time of the calculation of the SPR signal, the extraction means 19 extracts a pixel row Y, which contains the abnormal pixel. The adverse effects of the abnormal pixel are thus eliminated, and the SPR signal is calculated. By way of example, the non-uniformity of the interface 10b occurs due to non-uniformity of the ligand acting as the sensing medium, which has been fixed to the metal film 12. The non-uniformity of the ligand may occur due to, for example, non-uniformity occurring at the time of the fixation, or non-uniformity, which is caused to occur by partial peeling off at the time of buffer introduction and washing for sensitivity calibration.

An example of how the abnormal pixel row is extracted by the extraction means 19 will be described hereinbelow. Firstly, an example of how the abnormal pixel row is extracted by use of the output (intensity) distribution profiles of the pixel columns of the CCD image sensor 17, which pixel columns stand side by side with respect to the incidence angle direction X, will be described hereinbelow.

Figure 3A:
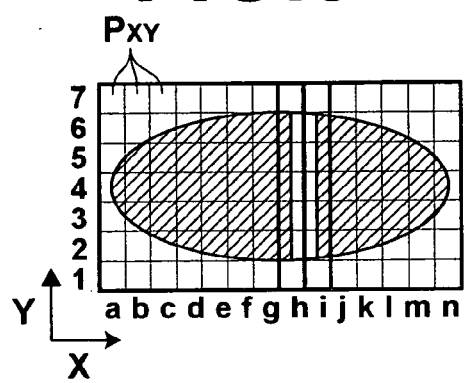
FIG. 3A is an explanatory view showing an image formed by the light beam, which image is detected by the photo detecting means in cases where the optical path is free from defects.
Figure 3A:
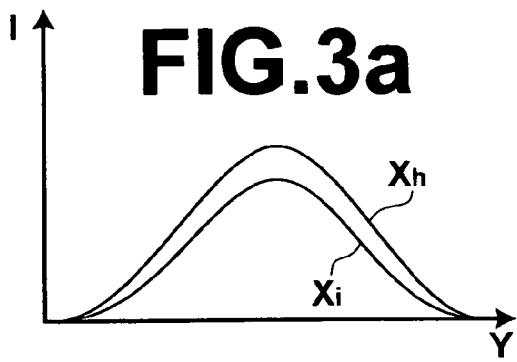
Figure 3B:
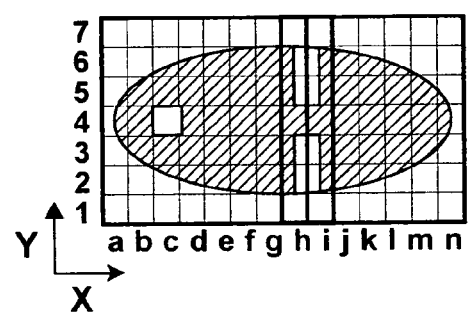
FIG. 3B is an explanatory view showing an image formed by the light beam, which image is detected by the photo detecting means in cases where non-uniform part is present on the optical path.
Figure 3B:
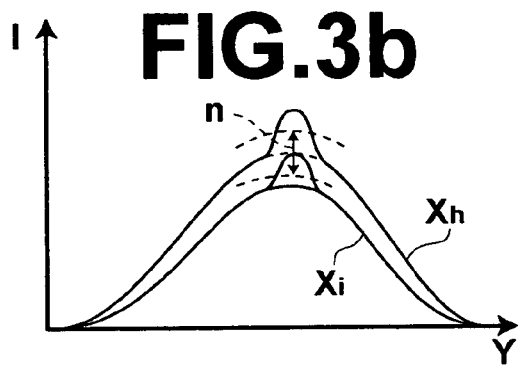

FIG. 3A is an explanatory view showing an image formed by the laser beam 13, which image is detected by the CCD image sensor 17 in cases where the optical path is free from defects. FIG. 3a is a graph showing the intensity distribution profiles of the pixel columns Xh and Xi in the image shown in FIG. 3A, which pixel columns stand side by side with respect to the incidence angle direction X and along which pixel columns a dark line has been detected, the intensity distribution profiles being taken in the beam width direction Y. FIG. 3B is an explanatory view showing an image formed by the laser beam 13, which image is detected by the CCD image sensor 17 in cases where non-uniform part is present on the optical path, e.g. in cases where non-uniform part is present on the interface 10b. FIG. 3b is a graph showing the intensity distribution profiles of the pixel columns Xh and Xi in the image shown in FIG. 3B, which pixel columns stand side by side with respect to the incidence angle direction X and along which pixel columns a dark line has been detected, the intensity distribution profiles being taken in the beam width direction Y.

As illustrated in FIG. 3B, in cases where the non-uniform part is present on the optical path, adverse effects occur such that, for example, part of the dark line D appears at a different position. As illustrated in FIG. 3a, in cases where the image of the laser beam 13 illustrated in FIG. 3A is detected, each of the intensity distribution profiles of the pixel columns Xh and Xi containing the dark line D, each of which intensity distribution profiles is obtained from the pixel data of the pixels arrayed in the beam width direction Y, takes on the form of the approximately perpendicular distribution. Also, as illustrated in FIG. 3b, in cases where the image of the laser beam 13 illustrated in FIG. 3B is detected, each of the intensity distribution profiles of the pixel columns Xh and Xi containing the dark line D, each of which intensity distribution profiles is obtained from the pixel data of the pixels arrayed in the beam width direction Y, contains part deviating from the normal distribution (indicated by the broken line in FIG. 3b).

Therefore, a fitting process with the normal distribution is performed on the intensity distribution profiles of the pixel columns Xh and Xi, along which pixel columns the dark line D has been detected, the intensity distribution profiles being taken in the beam width direction Y. Also, a pixel associated with a rate of deviation from the normal distribution, which rate of deviation is higher than a predetermined value, is detected as an abnormal pixel. Further, the pixel row Y4, which contains the abnormal pixel, is extracted as the abnormal pixel row. In the cases of the example shown in FIG. 3b, the pixels $P_{h4}$ and $P_{i4}$ associated with the rates of deviation from the normal distribution n, which rates of deviation are equal to at least 10% (i.e., which rates of deviation do not fall within the range indicated by the double headed arrow in FIG. 3b), are taken as the abnormal pixels, and the pixel row Y4, which contains the abnormal pixels $P_{h4}$ and $P_{i4}$, is extracted as the abnormal pixel row. In such cases, the pixel data representing the pixels, which are contained in the pixel row Y4, are excluded from the calculation of the SPR signal. The extraction of the abnormal pixel row is identical with the extraction of the normal pixel rows. Specifically, only the pixels associated with the rates of deviation from the normal distribution, which rates of deviation are smaller than the predetermined value, may be detected as the normal pixels, and the pixel rows containing the normal pixels may be extracted as the normal pixel rows. The pixel data obtained from the pixels arrayed along the pixel rows Y1 and Y7, which receive little image region of the laser beam 13, may be utilized for the calculation of the SPR signal. Alternatively, the pixel data obtained from the pixels arrayed along the pixel rows Y1 and Y7, may be excluded from the calculation of the SPR signal.

In the signal processing section 20, the aforesaid processing with the extraction means 19 may be performed at the time of the acquisition of the SPR signal, the SPR signal may be calculated in accordance with the outputs of the pixels other than the abnormal pixels. In cases where the alteration of the state of the binding of one substance to be analyzed is to be measured, at the time of the first process for the acquisition of the SPR signal with respect to the substance to be analyzed, the aforesaid processing with the extraction means 19 may be performed in order to extract the abnormal pixel row.

Ordinarily, before the analysis with respect to the substance to be analyzed is performed, an analysis with respect to a reference liquid sample is performed for sensitivity calibration. In such cases, at the time of the acquisition of the SPR signal with respect to the reference liquid sample, the extraction of the abnormal pixel row may be performed in the manner described above, and the SPR signal may be acquired from the pixel data of the pixels other than the pixels arrayed along the abnormal pixel row. In this manner, the accuracy of the sensitivity calibration is capable of being enhanced. In cases where the abnormal pixel row has been extracted at the time of the analysis with respect to the reference liquid sample, the calculation of the SPR signal at the time of the analysis with respect to the substance to be analyzed may be made in accordance with the outputs obtained from the pixel rows other than the abnormal pixel row, which has been extracted by the extraction means 19 at the time of the acquisition of the SPR signal with respect to the reference liquid sample.

A different example of how the abnormal pixel row is extracted by the extraction means 19 will be described hereinbelow.

As described above, ordinarily, before the analysis with respect to the substance to be analyzed is performed, the SPR signal with respect to a reference liquid sample, whose refractive index is known, is acquired for the sensitivity calibration, and a sensitivity calibration value is calculated.

In this example, for the sensitivity calibration, the SPR signal is acquired with respect to each of three kinds of reference liquid samples A, B, C, whose refractive indexes are known previously.

In the surface plasmon resonance analysis apparatus 1, each of the outputs obtained from the light receiving devices of the CCD image sensor 17 is the voltage V in accordance with the received light intensity. The difference value between the outputs, which are obtained from the two pixel columns located in the vicinity of the dark line D, is taken as the SPR signal. Also, the alteration of the position of the attenuated total reflection (i.e., the alteration of the refractive index) is calculated from the SPR signal. The signal value of the SPR signal is set so as to have the proportional relationship with the refractive index. However, the inclination of the SPR signal depends upon the apparatus and the analysis chip. Therefore, before the analysis with respect to each of the substances to be analyzed is made, the inclination of the SPR signal is measured. By use of the measured inclination of the SPR signal, the sensitivity calibration is made, and the result of the analysis with respect to the substance to be analyzed is obtained.

Figure 4:
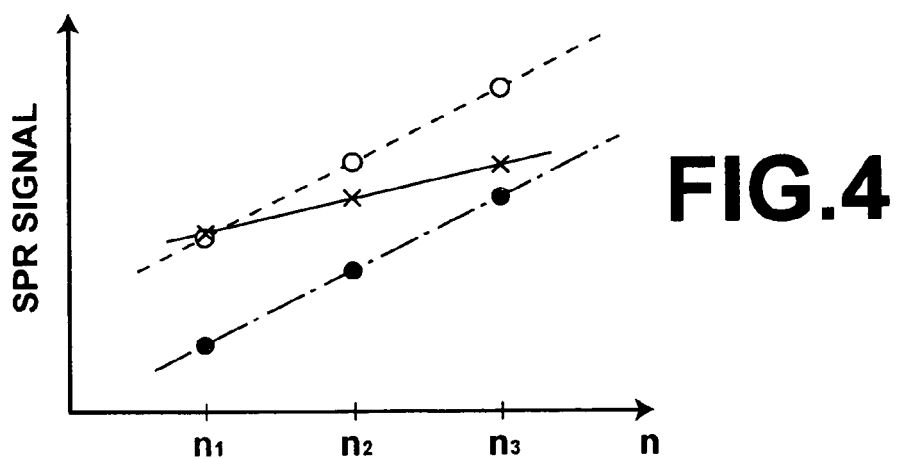
FIG. 4 is a graph showing relationship between an SPR signal and a refractive index, which relationship is utilized for the calculation of a calibration value.

Specifically, the SPR signal is acquired with respect to each of the reference liquid sample A having a known refractive index n1, the reference liquid sample B having a known refractive index n2, and the reference liquid sample C having a known refractive index n3 (wherein n1<n2<n3 and n3−n2=n2−n1=Δn). Also, the alteration of the SPR signal with respect to the alteration of the refractive index is calculated. At the time of the sensitivity calibration, the analysis chip 9 for the analysis of the substance to be analyzed is used. The reference liquid sample A having the refractive index n1 is firstly introduced into the analysis chip 9, and the SPR signal with respect to the reference liquid sample A is acquired. The reference liquid sample A is then sucked up from the analysis chip 9, and the analysis chip 9 is washed. Thereafter, the reference liquid sample B having the refractive index n2 is introduced into the analysis chip 9, and the SPR signal with respect to the reference liquid sample B is acquired. The reference liquid sample B is then sucked up from the analysis chip 9, and the analysis chip 9 is washed. Thereafter, the reference liquid sample C having the refractive index n3 is introduced into the analysis chip 9, and the SPR signal with respect to the reference liquid sample C is acquired. The relationship between the SPR signal and the refractive index is shown in FIG. 4. The inclination of the SPR signal is calculated as the calibration value.

Heretofore, in cases where the calibration value is to be obtained with the technique described above, the SPR signal has been calculated from the outputs obtained from all of the light beam components, which are taken in the beam width direction Y. Therefore, with the conventional technique, in cases where the profile taken in the beam width direction Y contains abnormality, a measured value, which contains the data of the abnormal part, is obtained. Specifically, incases where the profile taken in the beam width direction Y is free from abnormality, the inclination of the SPR signal with respect to the alteration of the refractive index among n1, n2, and n3 may be represented by the broken line connecting the white dots (indicated by the "○" mark) in FIG. 4. However, if abnormality, e.g. peeling off of part of the ligand, occurs between the measurement for the reference liquid sample A and the measurement for the reference liquid sample B, the inclination represented by, for example, the solid line connecting the "x" marks in FIG. 4 will be obtained as the calibration value due to the adverse effects of the abnormality.

Therefore, with respect to each of the pixel rows Y1, Y2, Y3, . . . , Y7, the extraction means 19 calculates the alteration of the position of the dark line, which alteration occurs at the time of the measurements for the reference liquid sample A having the refractive index n1, the reference liquid sample B having the refractive index n2, and the reference liquid sample C having the refractive index n3. Also, the extraction means 19 extracts a pixel row, which is associated with an alteration of the position of the dark line different from the ideal alteration obtained from the difference in refractive index, as the abnormal pixel row. Specifically, the extraction means 19 calculates the inclination of the SPR signal from each of the pixel rows Y1, Y2, Y3, . . . , Y7, and extracts the pixel row, which is associated with an inclination value falling outside a predetermined range, as the abnormal pixel row. Also, the extraction means 19 utilizes only the outputs obtained from the pixel rows, which are associated with an inclination value falling within the predetermined range, for the calculation of the calibration value. In cases where the outputs, which have been obtained from the pixels arrayed along the abnormal pixel row Y, are excluded from the outputs, which have been obtained from the pixels arrayed along the adjacent pixel columns X containing the dark line, and the difference between the outputs obtained from the adjacent pixel columns X, the signal values become low as indicated by the single-dot chained line connecting the black dots (indicated by the "●" mark) in FIG. 4. However, in such cases, the inclination free from the adverse effects of the abnormal pixel is capable of being obtained.

With the extraction means 19, since the differences in refractive index among the reference liquid samples A, B, and C are known, the ideal value of the aforesaid inclination is capable of being calculated. Therefore, in accordance with the ideal value of the inclination, the pixel row, which is associated with an inclination value falling outside the predetermined range, is capable of being extracted as the abnormal pixel row. Also, the normal pixel rows will exhibit the alteration in accordance with the differences in refractive index and will exhibit an approximately identical inclination. Therefore, the inclinations exhibited by the pixel rows may be compared with one another, and a pixel row, which exhibits an inclination markedly different from the aforesaid approximately identical inclination having been obtained from the majority of the pixel rows, may be extracted as the abnormal pixel row. In cases where the image of the laser beam 13 illustrated in FIG. 3B is detected, the pixel rows Y1 and Y7, which receive little laser beam, are regarded as the abnormal pixel rows.

As described above, at the time of the acquisition of the SPR signals with respect to the reference liquid samples for the sensitivity calibration, the abnormal pixel row Y is extracted by the extraction means 19. Also, at the time of the measurement with respect to the substance to be analyzed, the SPR signal is calculated in accordance with the pixel data other than the pixel data of the abnormal pixel row Y.

As described above, with the surface plasmon resonance analysis apparatus 1, the abnormal pixel row is extracted by the extraction means 19, and the SPR signal is detected in accordance with the pixel data of the pixel rows other than the abnormal pixel row. Therefore, in cases where defects occur at part of the optical path, and the dark line profile becomes deformed, the accurate measurement result is capable of being obtained without being affected adversely by the defects.

In the embodiment described above, the CCD image sensor 17 comprising the plurality of the light receiving devices arrayed in the two-dimensional directions composed of the beam width direction and the incidence angle direction is employed as the photo detecting means. Alternatively, a photodiode array comprising a plurality of photodiodes arrayed in the two-dimensional directions may be employed as the photo detecting means.

A second embodiment of the analysis apparatus utilizing attenuated total reflection in accordance with the present invention, which is constituted as a surface plasmon resonance analysis apparatus 101 and which is provided with different photo detecting means, will be described herein below. FIG. 5A is a schematic side view showing a second embodiment of the analysis apparatus utilizing attenuated total reflection in accordance with the present invention, which is constituted as the surface plasmon resonance analysis apparatus 101. FIG. 5B is an explanatory plan view showing a direction of movement of a light receiving section 71 of photo detecting means 70 utilized in the surface plasmon resonance analysis apparatus of FIG. 5A. In FIG. 5A, similar elements are numbered with the same reference numerals with respect to FIG. 1A.

With reference to FIG. 5A, the photo detecting means 70 is provided with the light receiving section 71, which comprises a plurality of light receiving devices 71a, 71a, . . . arrayed in the beam width direction. The photo detecting means 70 is also provided with a movement section for moving the light receiving section 71 in the incidence angle direction. In this manner, the light receiving section 71, which may be provided with one pixel column or several pixel columns, may be moved by the movement section and in the incidence angle direction, and the two-dimensional beam image may thereby be obtained.

The light receiving section 71 is secured to a moving base 80. An internal thread block 82, which is engaged with a precision screw 81 extending in the incidence angle direction X, is secured to the moving base 80. The moving base 80 is supported by guide means (not shown) such that the moving base 80 is capable of moving in parallel with the longitudinal axis of the precision screw 81. Opposite ends of the precision screw 81 are supported for movement by two support sections 84, 84, which are secured to a secured base 83. One of the opposite ends of the precision screw 81 is connected to a driving shaft of a stepping motor 85, which is capable of rotating in clockwise and counter-clockwise directions. Therefore, when the precision screw 81 is rotated by the stepping motor 85, the internal thread block 82 moves in the incidence angle direction X, and the light receiving section 71 secured to the moving base 80 moves linearly in the incidence angle direction X. In this embodiment, the movement means for moving the light receiving section 71 is constituted of the moving base 80, the precision screw 81, the internal thread block 82, the secured base 83, the support sections 84, 84, and the stepping motor 85.

The position of the moving base 80, i.e. the position of the light receiving section 71, with respect to the incidence angle direction X is detected by an encoder 86, which acts as position detecting means. The output from the light receiving section 71 and the corresponding output signal, which is outputted from the encoder 86 and represents the detected position, are processed in the signal processing section 20 for the formation of the two-dimensional image performed in the same manner as that for the two-dimensional image acquired from the CCD image sensor 17 employed in the first embodiment described above.

Figures 6A, 6B:
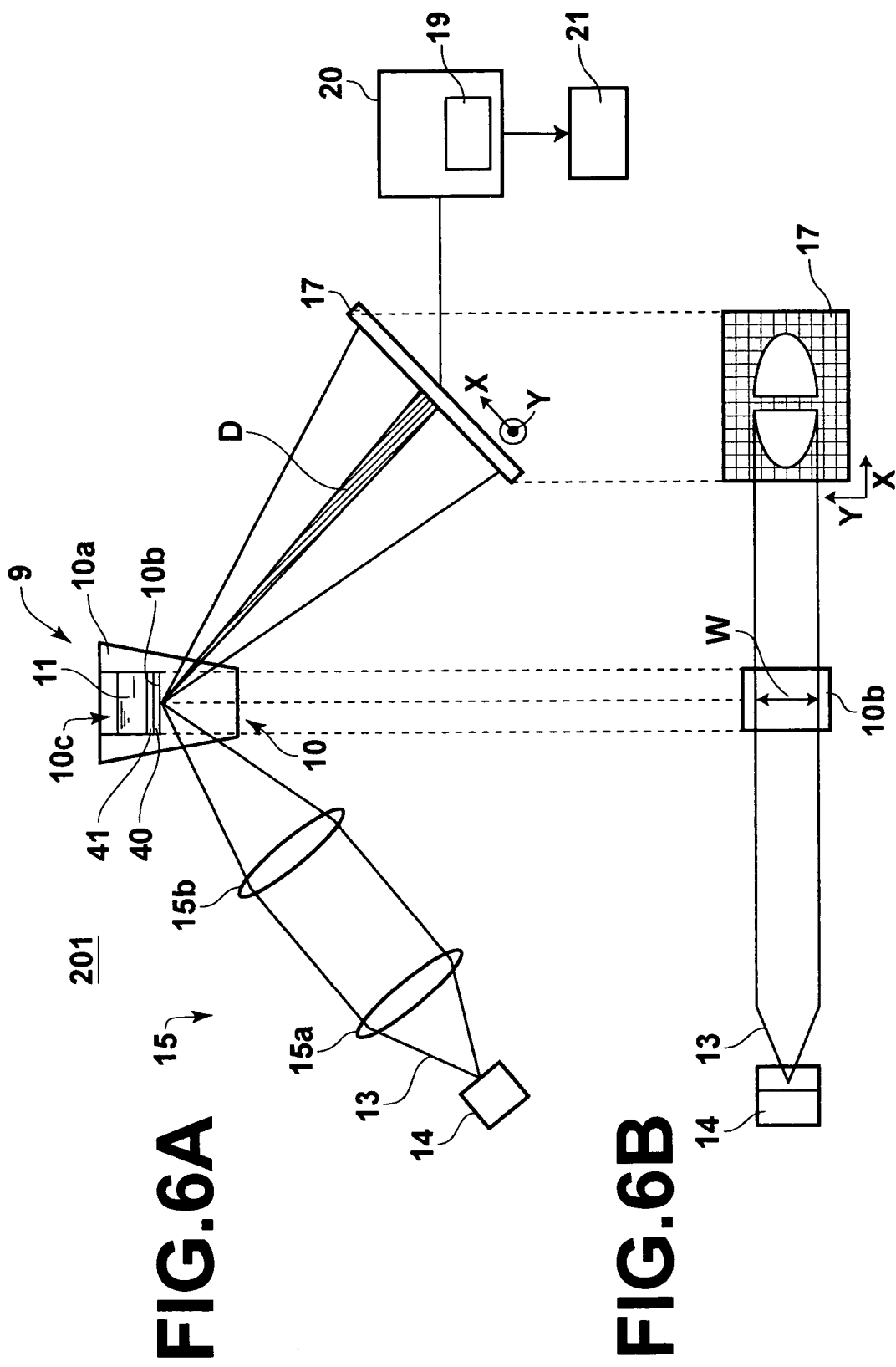
FIG. 6A is a schematic side view showing a third embodiment of the analysis apparatus utilizing attenuated total reflection in accordance with the present invention, which is constituted as a leaky mode analysis apparatus.
FIG. 6B is an explanatory plan view showing an optical path in the leaky mode analysis apparatus of FIG. 6A and an image formed by a light beam on a light receiving surface of the photo detecting means.

The surface plasmon resonance analysis apparatus described above may be constituted as a leaky mode analysis apparatus 201 through modification of part of the constitution. FIG. 6A is a schematic side view showing a third embodiment of the analysis apparatus utilizing attenuated total reflection in accordance with the present invention, which is constituted as the leaky mode analysis apparatus 201. FIG. 6B is an explanatory plan view showing an optical path in the leaky mode analysis apparatus 201 of FIG. 6A and an image formed by a light beam on a light receiving surface of the photo detecting means. In FIG. 6A, similar elements are numbered with the same reference numerals with respect to FIG. 1A.

As in the cases of the surface plasmon resonance analysis apparatus described above, the leaky mode analysis apparatus 201 utilizes the analysis chip 9. A cladding layer 40 is formed on the bottom surface of the recess 10c of the analysis chip 9, and an optical waveguide layer 41 is formed on the cladding layer 40. In this embodiment, the thin film layer is constituted of the combination of the cladding layer 40 and the optical waveguide layer 41.

By way of example, the dielectric material block 10 is made from a synthetic resin or optical glass, such as BK7. The cladding layer 40 is formed in a thin film-like shape by use of a dielectric material having a refractive index lower than the refractive index of the dielectric material block 10, or a metal, such as gold. The optical waveguide layer 41 is formed in a thin film-like shape by use of a dielectric material, such as PMMA, having a refractive index higher than the refractive index of the cladding layer 40. In cases where the cladding layer 40 is constituted of a thin gold film, the film thickness of the cladding layer 40 may be approximately 36.5 nm. In cases where the optical waveguide layer 41 is constituted of PMMA, the film thickness of the optical waveguide layer 41 may be approximately 700 nm.

With the leaky mode analysis apparatus 201 having the constitution described above, in cases where the laser beam 13 having been produced by the laser beam source 14 passes through the dielectric material block 10 and impinges upon the cladding layer 40 at an incidence angle, which is not smaller than the total reflection angle, a majority of the laser beam 13 is totally reflected from the interface 10b between the dielectric material block 10 and the cladding layer 40. However, the light of a specific wave number, which has passed through the cladding layer 40 and has impinged upon the optical waveguide layer 41 at a specific incidence angle, is propagated in a guided mode through the optical waveguide layer 41. In cases where the guided mode is thus excited, the majority of the incident light having impinged upon the optical waveguide layer 41 at the specific incidence angle is taken into the optical waveguide layer 41. Therefore, the intensity of the light, which has impinged upon the interface 10b at the specific incidence angle and has been totally reflected from the interface 10b, becomes markedly low, and the attenuated total reflection thus occurs.

The wave number of the guided optical wave in the optical waveguide layer 41 depends upon the refractive index of the liquid sample 11, which is located on the optical waveguide layer 41. Therefore, in cases where the aforesaid specific incidence angle, which is associated with the occurrence of the attenuated total reflection, i.e. the ATR angle, is detected, the refractive index of the liquid sample 11 and characteristics of the liquid sample 11 with regard to the refractive index of the liquid sample 11 are capable of being analyzed. With the leaky mode analysis apparatus 201, by the provision of the photo detecting means, which is capable of acquiring the two-dimensional image, and the signal processing section 20, which is provided with the extraction means 19 and which calculates the position of the dark line by excluding the abnormal pixel data, the lowering of the sensitivity due to non-uniformity of part of the analysis chip 9 or due to staining of part of the optical system, or the like, is capable of being suppressed, and the position of the dark line (the alteration of the dark line) is capable of being detected accurately.

In the embodiments described above, the analysis chip is constituted of the dielectric material block provided with one sample support section. Also, in cases where a sensor unit (an analysis plate) is constituted of a dielectric material block and a plurality of sample support sections, which are located in a one-dimensional direction or in two-dimensional directions on the dielectric material block, the combination of one sample support section and the corresponding region of the dielectric material block may be regarded as one analysis chip. The sensor unit described above is described in, for example, Japanese Unexamined Patent Publication No. 2003-202285. Alternatively, the sample support section and the dielectric material block may be constituted as two independent sections.

As another alternative, a flow path type of analysis chip as illustrated in FIG. 7 and FIG. 8 may be employed. FIG. 7 is a front view showing an example of a sensor unit, which is provided with a plurality of flow path types of analysis chips. FIG. 8 is a sectional view showing part of the sensor unit of FIG. 7.

With reference to FIG. 7 and FIG. 8, a sensor unit 100 comprises a dielectric material block (a main body) 110, which is transparent with respect to a light beam. The dielectric material block 110 has a smooth top surface 110a. A metal film 112 acting as the thin film layer is formed on the top surface 110a of the dielectric material block 110. The sensor unit 100 also comprises a flow path member 115, which is in close contact with the top surface of the metal film 112 having been formed on the dielectric material block 110.

The flow path member 115 is provided with a plurality of flow paths 116, 116, . . . , each of which extends in the longitudinal direction of the flow path member 115. Each of the flow paths 116, 116, . . . is constituted of a supply path 116b and a discharging path 116d. The supply path 116b extends from an inlet 116a to a measurement path 116c. The discharging path 116d extends from the measurement path 116c to an outlet 116e. The plurality of the flow paths 116, 116, . . . are located along a straight line.

As illustrated in FIG. 8, an outlet of the supply path 116b and an inlet of the discharging path 116d are open at the bottom area of the flow path member 115. Also, a sealing section 115a is formed at the area of the bottom of the flow path member 115, which area comes into contact with the surface of the metal film 112. The sealing section 115a surrounds the outlet of the supply path 116b and the inlet of the discharging path 116d. The measurement path 116c is formed at the inside of the space defined by the sealing section 115a. Therefore, in cases where the flow path member 115 is brought into close contact with the top surface of the metal film 112 of the dielectric material block 110, the measurement path 116c, which is formed at the inside of the space defined by the sealing section 115a, acts as the flow path. Specifically, the flow path member 115 acts as the sample support section. The sealing section 115a may be combined with the top part of the flow path member 115 (at which top part the supply path 116b and the discharging path 116d are formed) into an integral body. Alternatively, the sealing section 115a may be made from a material different from the material of the top part of the flow path member 115 and may be fitted to the top part of the flow path member 115. By way of example, an O-ring acting as the sealing section 115a may be fitted to the bottom part of the flow path member 115. In the cases of the sensor unit 100 described above, the combination of one flow path 116 and the corresponding region of the dielectric material block 110 constitutes one analysis chip.

In the cases of the sensor unit 100, it is assumed that a liquid sample containing a protein is used. However, if the protein contained in the liquid sample fixes to the flow path 116, the analysis will not be capable of being made accurately. Therefore, the flow path member 115 should preferably be made from a material, which does not have non-specific adsorption characteristics with respect to proteins. Specifically, the flow path member 115 should preferably be made from a material, such as silicon or a polypropylene.

A sample may be supplied into the sensor unit 100 in the manner described below. Specifically, a sample supplying pipette tip is inserted into the inlet 116a of the flow path member 115, and a sample sucking pipette tip is inserted into the outlet 116e of the flow path member 115. Also, the sample is supplied from the sample supplying pipette tip into the measurement path 116c of the flow path 116.

In the sensor unit 100 described above, the flow path member 115 is provided with the plurality of the flow paths 116, 116, . . . , which are located along the straight line. Alternatively, a flow path member provided with only one flow path 116 may be employed. As another alternative, a flow path member provided with a plurality of flow paths 116, 116, . . . , which are located in a matrix-like pattern, may be employed.

As in the embodiments described above, the analysis apparatus utilizing the flow path type of the analysis chip may be provided with the photo detecting means, which is capable of acquiring the two-dimensional image, and the signal processing section, which comprises the extraction means and which calculates the position of the dark line by excluding the abnormal pixel data. With the analysis apparatus utilizing the flow path type of the analysis chip, by the provision of the photo detecting means and the signal processing section, the lowering of the sensitivity due to non-uniformity of part of the analysis chip or due to staining of part of the optical system, or the like, is capable of being suppressed, and the position of the dark line (the alteration of the dark line) is capable of being detected accurately.

What is claimed is:

1. An analysis method utilizing attenuated total reflection, comprising the steps of:
   i) preparing an analysis chip, which is provided with a dielectric material block transparent with respect to a light beam having been produced by a light source, a thin film layer formed on one surface of the dielectric material block, and a sample support section for supporting a sample on a surface of the thin film layer,
   ii) irradiating the light beam, which has been produced by the light source, to the dielectric material block so as to have a predetermined beam width with respect to an interface between the dielectric material block and the thin film layer and at various different incidence angles such that a total reflection condition is satisfied at the interface between the dielectric material block and the thin film layer, and
   iii) measuring a position of a dark line in the light beam, which has been totally reflected from the interface between the dielectric material block and the thin film layer,
   wherein the measurement of the position of the dark line is performed with a process comprising:
   a) detecting an image of the light beam, which has been totally reflected from the interface between the dielectric material block and the thin film layer, with photo detecting means and as a two-dimensional image constituted of a plurality of pixels arrayed in two-dimensional directions composed of a beam width direction and an incidence angle direction, which are perpendicular to each other,
   b) extracting an abnormal pixel row, which contains a pixel represented by abnormal pixel data, from among pixel rows, which output pixel data that represent light intensity distribution profiles that indicate the light beam totally internally reflected at the interface and the dark line within the light beam, and each of which extends in the incidence angle direction, in the array of the pixels constituting the two-dimensional image and in accordance with an output obtained from the photo detecting means, which has detected the two-dimensional image with respect to the sample having been supported by the analysis chip, and
   c) calculating the position of the dark line with respect to the sample and in accordance with the pixel data corresponding to the pixel rows other than the abnormal pixel row, which has been extracted.

2. An analysis method utilizing attenuated total reflection, comprising the steps of:
   i) preparing an analysis chip, which is provided with a dielectric material block transparent with respect to a light beam having been produced by a light source, a thin film layer formed on one surface of the dielectric material block, and a sample support section for supporting a sample on a surface of the thin film layer,
   ii) irradiating the light beam, which has been produced by the light source, to the dielectric material block so as to have a predetermined beam width with respect to an interface between the dielectric material block and the thin film layer and at various different incidence angles such that a total reflection condition is satisfied at the interface between the dielectric material block and the thin film layer, and
   iii) measuring a position of a dark line in the light beam, which has been totally reflected from the interface between the dielectric material block and the thin film layer,
   wherein the measurement of the position of the dark line is performed with a process comprising:
   a) detecting an image of the light beam, which has been totally reflected from the interface between the dielectric material block and the thin film layer, with photo detecting means and as a two-dimensional image constituted of a plurality of pixels arrayed in two-dimensional directions composed of a beam width direction and an incidence angle direction, which are perpendicular to each other,
   b) extracting an abnormal pixel row, which contains a pixel represented by abnormal pixel data, from among pixel rows, which output pixel data that represent light intensity distribution profiles that indicate the light beam totally internally reflected at the interface and the dark line within the light beam, and each of which extends in the incidence angle direction, in the array of the pixels constituting the two-dimensional image and in accordance with an output obtained from the photo detecting means, which has detected the two-dimensional image with respect to a reference sample having been supported by the analysis chip, and c) calculating the position of the dark line with respect to the reference sample and in accordance with the pixel data corresponding to the pixel rows other than the abnormal pixel row, which has been extracted.

3. A method as defined in claim 1 wherein the extraction of the abnormal pixel row, which contains the pixel represented by the abnormal pixel data, is performed with a process for:

forming an output distribution profile of each of pixel columns, each of which extends in the beam width direction, in the array of the pixels constituting the two-dimensional image and in accordance with the output obtained from the photo detecting means, comparing the output distribution profile and a normal distribution with each other, detecting a pixel associated with a rate of deviation from the normal distribution, which rate of deviation is higher than a predetermined value, and extracting a pixel row extending in the incidence angle direction, which pixel row contains the thus detected pixel, as the abnormal pixel row.

4. A method as defined in claim 2 wherein the extraction of the abnormal pixel row, which contains the pixel represented by the abnormal pixel data, is performed with a process for:

forming an output distribution profile of each of pixel columns, each of which extends in the beam width direction, in the array of the pixels constituting the two-dimensional image and in accordance with the output obtained from the photo detecting means, comparing the output distribution profile and a normal distribution with each other, detecting a pixel associated with a rate of deviation from the normal distribution, which rate of deviation is higher than a predetermined value, and extracting a pixel row extending in the incidence angle direction, which pixel row contains the thus detected pixel, as the abnormal pixel row.

5. A method as defined in claim 2 wherein the extraction of the abnormal pixel row, which contains the pixel represented by the abnormal pixel data, is performed with a process for:

obtaining the output from the photo detecting means and with respect to each of a plurality of reference samples, differences in refractive index among the plurality of the reference samples being known previously, calculating an alteration of the position of the dark line with respect to the incidence angle direction, which alteration occurs in each of the pixel rows extending in the incidence angle direction, detecting a pixel row associated with the alteration of the position of the dark line with respect to the incidence angle direction, which alteration varies from an ideal alteration obtained from the differences in refractive index among the plurality of the reference samples, and extracting the thus detected pixel row as the abnormal pixel row.

6. A method as defined in claim 1 wherein the photo detecting means comprises a plurality of light receiving devices, which are arrayed in the two-dimensional directions composed of the beam width direction and the incidence angle direction.

7. A method as defined in claim 2 wherein the photo detecting means comprises a plurality of light receiving devices, which are arrayed in the two-dimensional directions composed of the beam width direction and the incidence angle direction.

8. A method as defined in claim 1 wherein the photo detecting means comprises a light receiving section, which is provided with a plurality of light receiving devices arrayed in the beam width direction, and a movement section for moving the light receiving section in the incidence angle direction.

9. A method as defined in claim 2 wherein the photo detecting means comprises a light receiving section, which is provided with a plurality of light receiving devices arrayed in the beam width direction, and a movement section for moving the light receiving section in the incidence angle direction.

10. An analysis apparatus utilizing attenuated total reflection, comprising:

i) a light source for producing a light beam, ii) an analysis chip, which is provided with a dielectric material block transparent with respect to the light beam having been produced by the light source, a thin film layer formed on one surface of the dielectric material block, and a sample support section for supporting a sample on a surface of the thin film layer, iii) a light beam irradiating optical system for irradiating the light beam, which has been produced by the light source, to the dielectric material block so as to have a predetermined beam width with respect to an interface between the dielectric material block and the thin film layer and at various different incidence angles such that a total reflection condition is satisfied at the interface between the dielectric material block and the thin film layer, and iv) measurement means for measuring a position of a dark line in the light beam, which has been totally reflected from the interface between the dielectric material block and the thin film layer, wherein the measurement means is provided with:

a) photo detecting means for detecting an image of the light beam, which has been totally reflected from the interface between the dielectric material block and the thin film layer, as a two-dimensional image constituted of a plurality of pixels arrayed in two-dimensional directions composed of a beam width direction and an incidence angle direction, which are perpendicular to each other, and b) extraction means for extracting an abnormal pixel row, which contains a pixel represented by abnormal pixel data, from among pixel rows, which output pixel data that represent light intensity distribution profiles that indicate the light beam totally internally reflected at the interface and the dark line within the light beam, and each of which extends in the incidence angle direction, in the array of the pixels constituting the two-dimensional image and in accordance with an output obtained from the photo detecting means, which has detected the two-dimensional image with respect to the sample having been supported by the analysis chip, and the measurement means calculates the position of the dark line with respect to the sample and in accordance with the pixel data corresponding to the pixel rows other than the abnormal pixel row, which has been extracted by the extraction means.

11. An analysis apparatus utilizing attenuated total reflection, comprising:

i) a light source for producing a light beam, ii) an analysis chip, which is provided with a dielectric material block transparent with respect to the light beam having been produced by the light source, a thin film layer formed on one surface of the dielectric material block, and a sample support section for supporting a sample on a surface of the thin film layer, iii) a light beam irradiating optical system for irradiating the light beam, which has been produced by the light source, to the dielectric material block so as to have a predetermined beam width with respect to an interface between the dielectric material block and the thin film layer and at various different incidence angles such that a total reflection condition is satisfied at the interface between the dielectric material block and the thin film layer, and iv) measurement means for measuring a position of a dark line in the light beam, which has been totally reflected from the interface between the dielectric material block and the thin film layer, wherein the measurement means is provided with:

a) photo detecting means for detecting an image of the light beam, which has been totally reflected from the interface between the dielectric material block and the thin film layer, as a two-dimensional image constituted of a plurality of pixels arrayed in two-dimensional directions composed of a beam width direction and an incidence angle direction, which are perpendicular to each other, and b) extraction means for extracting an abnormal pixel row, which contains a pixel represented by abnormal pixel data, from among pixel rows, which output pixel data that represent light intensity distribution profiles that indicate the light beam totally internally reflected at the interface and the dark line within the light beam, and each of which extends in the incidence angle direction, in the array of the pixels constituting the two-dimensional image and in accordance with an output obtained from the photo detecting means, which has detected the two-dimensional image with respect to a reference sample having been supported by the analysis chip, and the measurement means calculates the position of the dark line with respect to the reference sample and in accordance with the pixel data corresponding to the pixel rows other than the abnormal pixel row, which has been extracted by the extraction means.

12. An apparatus as defined in claim 10 wherein the extraction means performs a process for:

forming an output distribution profile of each of pixel columns, each of which extends in the beam width direction, in the array of the pixels constituting the two-dimensional image and in accordance with the output obtained from the photo detecting means, comparing the output distribution profile and a normal distribution with each other, detecting a pixel associated with a rate of deviation from the normal distribution, which rate of deviation is higher than a predetermined value, and extracting a pixel row extending in the incidence angle direction, which pixel row contains the thus detected pixel, as the abnormal pixel row.

13. An apparatus as defined in claim 11 wherein the extraction means performs a process for:

forming an output distribution profile of each of pixel columns, each of which extends in the beam width direction, in the array of the pixels constituting the two-dimensional image and in accordance with the output obtained from the photo detecting means, comparing the output distribution profile and a normal distribution with each other, detecting a pixel associated with a rate of deviation from the normal distribution, which rate of deviation is higher than a predetermined value, and extracting a pixel row extending in the incidence angle direction, which pixel row contains the thus detected pixel, as the abnormal pixel row.

14. An apparatus as defined in claim 11 wherein the extraction means performs a process for:

obtaining the output from the photo detecting means and with respect to each of a plurality of reference samples, differences in refractive index among the plurality of the reference samples being known previously, calculating an alteration of the position of the dark line with respect to the incidence angle direction, which alteration occurs in each of the pixel rows extending in the incidence angle direction, detecting a pixel row associated with the alteration of the position of the dark line with respect to the incidence angle direction, which alteration varies from an ideal alteration obtained from the differences in refractive index among the plurality of the reference samples, and extracting the thus detected pixel row as the abnormal pixel row.

15. An apparatus as defined in claim 10 wherein the photo detecting means comprises a plurality of light receiving devices, which are arrayed in the two-dimensional directions composed of the beam width direction and the incidence angle direction.

16. An apparatus as defined in claim 11 wherein the photo detecting means comprises a plurality of light receiving devices, which are arrayed in the two-dimensional directions composed of the beam width direction and the incidence angle direction.

17. An apparatus as defined in claim 10 wherein the photo detecting means comprises a light receiving section, which is provided with a plurality of light receiving devices arrayed in the beam width direction, and a movement section for moving the light receiving section in the incidence angle direction.

18. An apparatus as defined in claim 11 wherein the photo detecting means comprises a light receiving section, which is provided with a plurality of light receiving devices arrayed in the beam width direction, and a movement section for moving the light receiving section in the incidence angle direction.

19. A method as defined in claim 1, wherein the light beam is a linear beam which impinges upon the interface between the dielectric material block and the thin film layer so as to have the predetermined beam width extending in the beam width direction.

20. A method as defined in claim 1, wherein extracting the abnormal pixel row includes calculating the inclination of a surface plasmon resonance signal from each of the pixel rows and extracting the abnormal pixel row, which is associated with an inclination value falling outside a predetermined range.

* * * * *